United States Patent [19]

Fujiwara et al.

[11] 4,343,991
[45] Aug. 10, 1982

[54] SAMPLE DETECTOR

[75] Inventors: Toshihide Fujiwara, Fuchu; Nobutaka Kaneko, Hachiouji, both of Japan

[73] Assignee: Olympus Optical Co., Ltd., Tokyo, Japan

[21] Appl. No.: 151,888

[22] Filed: May 21, 1980

[30] Foreign Application Priority Data

May 25, 1979 [JP] Japan ............................. 54-64817

[51] Int. Cl.³ ..................................... G01D 21/04
[52] U.S. Cl. ................................. 250/227; 250/548
[58] Field of Search ................... 250/227, 548, 568

[56] References Cited

U.S. PATENT DOCUMENTS 3,786,238  1/1974  Heisner ........................ 250/227 X
4,015,122  3/1977  Rubinstein ................... 250/227 X Primary Examiner—David C. Nelms
Assistant Examiner—Darwin R. Hostetter
Attorney, Agent, or Firm—Cushman, Darby & Cushman

[57] ABSTRACT

A sample detector is comprised of a first group of optical fibers having exit end surfaces arranged in the direction perpendicular to the shifting direction of the carrier, a second group of optical fibers having entrance end surfaces arranged opposite said exit end surfaces of the first group of optical fibers, a plural number of light emitting diodes arranged in the vicinity of the entrance end surfaces of the first group of optical fibers, a single photo detector element arranged in the vicinity of the exit end surfaces of the second group of optical fibers and a preamplifier connected to the output side of said photo detector element. Said sample detector is adapted in such a manner that the light emitting diodes are caused to glow consecutively, the light, having passed through the first group of optical fibers the carrier and the second group of optical fibers, is received by said photo-detector element, subjected to photoelectric conversion and amplified by said preamplifier. The presence of samples on the carrier is detected based on the outputs thus obtained.

3 Claims, 10 Drawing Figures

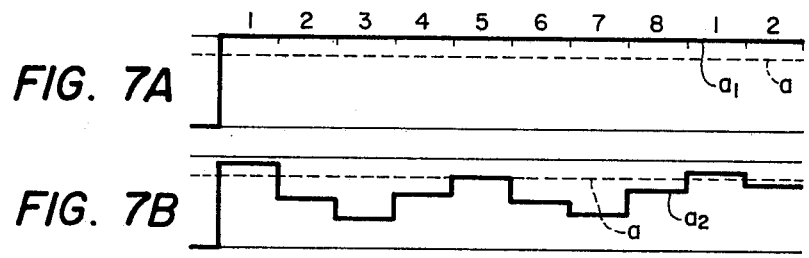
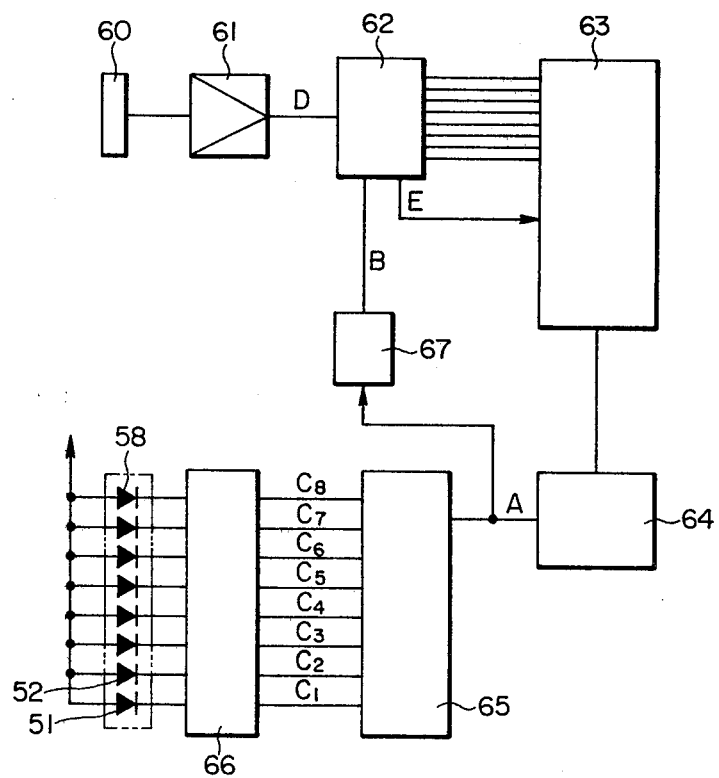

SAMPLE DETECTOR

BACKGROUND OF THE INVENTION (a) Field of the Invention

The present invention relates to a device for detecting positions of samples applied onto a carrier being shifted in a definite direction, and more specifically to a sample detector used for quantitative analyses of fractionated patterns of sera in electrophoresis.

(b) Description of the Prior Art

In the electrophoresis, samples are applied onto a carrier made of cellulose acetate paper or similar material and fractionated patterns of the samples are formed by electrically energizing the carrier. Then, the carrier is colored, discolored and made transparent by being dipped into a clarifying liquid, whereafter the fractionated patterns are quantitatively analyzed with a colorimeter. For automatic quantitative analyses of the sample applied onto the carrier with a colorimeter, the carrier is shifted between a light source and a photodetector, the carrier is stopped when a sample on the carrier is located right between the light source and photodetector, and the light source and photodetector are moved in the direction perpendicular to the shifting direction of the carrier to scan the sample for carrying out photometry. Such a photometric apparatus requires a sample detector which precisely detects a sample on the carrier to be subjected to photometery when it is located right between the light source and photodetector.

FIG. 1 shows the construction of an example of the conventionally known sample detectors. In this drawing, the reference numeral 1 represents a carrier, the reference numeral 2 designates fractionated patterns of samples applied at constant intervals on the carrier, the reference numeral 3 denotes a photometric light source assembly consisting of a light source lamp 4, a lens system 5, a filter 6, a slit plate 7, etc., the reference numeral 8 represents a photometric detector assembly consisting of a slit plate 9 and a photodetector element 10, the reference numeral 11 designates optical fibers having ends arranged in a row under the carrier passage and in the direction perpendicular to the shifting direction of the carrier as shown in FIG. 2, the reference numeral 12 denotes a light source lamp arranged at the other ends of the optical fibers 11, and the reference numeral 13 represents a plural number of photodetector elements arranged over the carrier passage for receiving light emerging through the optical fibers 11 from the light source lamp 12. These optical fibers 11, light source lamp 12 and photodetector elements 13 compose a sample detector.

When the carrier 1 is shifted in the direction indicated by the arrow A for photometry of samples in the photometric apparatus having the above-described construction, the light emerging from the optical fibers 11 pass through the carrier 1 and are received by the individual photodetector elements 13. The photodetector 13 provide high outputs when a transparent portion 1a of the carrier 1 corresponds to the position of the sample detector, and low outputs when the sample 2 applied onto the carrier 1 corresponds to said position. It is therefore possible to carry out photometry of the sample by stopping the shifting of the carrier 1 when the sample on the carrier is detected and shifting the photometric unit consisting of the light source assembly 3 and photometric detector 8 in the direction perpendicular to the shifting direction A of the carrier.

In the conventional sample detector having the above-described construction, each of the photodetector elements requires a preamplifier for processing signals obtained from the detector element, or highly priced preamplifiers having high imput impedance and low drift for signal processing with higher accuracy. Therefore, the conventional sample detector is unavoidably highly priced. In order to correct this defect, it is conceivable to use a single preamplifier in the conventional sample detector. For this purpose, however, it is necessary to use a single detector element which must have a photo sensitive area large enough to cover the end surfaces of many optical fibers at a time. Using a larger photosensitive area unavoidably increases dark current and drift, thereby degrading analytical accuracy. Furthermore, it is conceivable to use a single preamplifier in combination with a plural number of detector elements, but such a method requires a control circuit which selects a detector element to be connected to the preamplifier.

SUMMARY OF THE INVENTION

A general object of the present invention is to provide a sample detector manufacturable at a low cost and capable of detecting samples accurately comprising a plural number of light emitting elements, a first group of optical fibers having entrance ends arranged in the vicinity of the light emitting elements and exit ends arranged in a row in the direction perpendicular to the shifting direction of the carrier, a second group of optical fibers having entrance ends arranged opposite to the exit ends of the first group of optical fibers, a photodetector element arranged at the exit ends of the second group of optical fibers and a preamplifier for amplifying outputs from said photodetector element, said sample detector being adapted in such a manner that the individual light emitting elements are caused to glow consecutively. The light emitted from said elements is transferred through said first and second groups of optical fibers so as to be detected with the photodetector element, the detected signals are amplified by the preamplifier, and the presence of the carrier is detected based on the outputs thus obtained.

BRIEF DESCRIPTION OF THE DRAWINGS

FIG. 7A illustrates an example of the preamplifier outputs corresponding to a condition where no sample is detected;

FIG. 7B shows a diagram illustrating an example of the preamplifier outputs corresponding to a condition where a sample is detected;

FIG. 8 shows a block diagram of a circuit for data processing in the sample detector according to the present invention.

DETAILED DESCRIPTION OF THE PREFERRED EMBODIMENT

Figure 1:
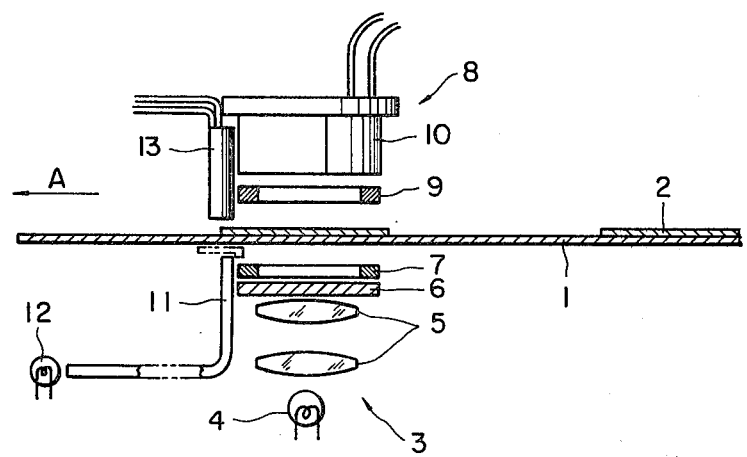
FIG. 1 shows a diagram illustrating the construction of the conventional sample detector.
Figure 2:
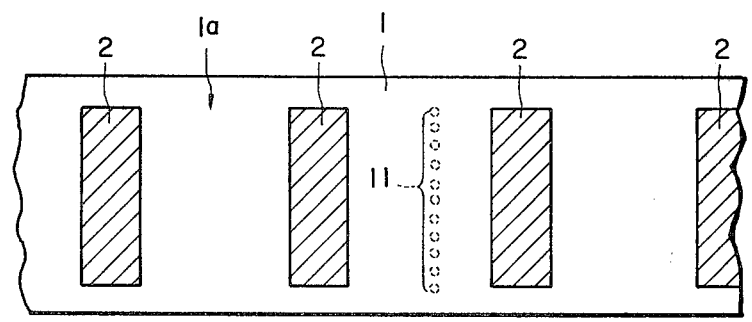
FIG. 2 shows a diagram illustrating the manner to shift a carrier with regard to optical fibers used in the sample detector.
Figure 3:
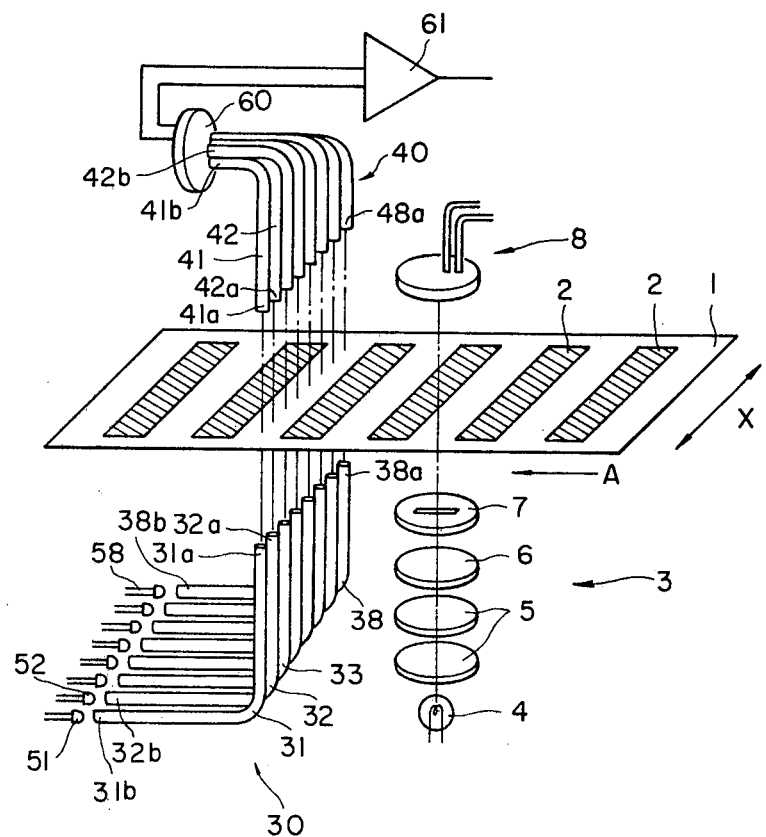
FIG. 3 shows a diagram illustrating construction of the sample detector according to the present invention.

An embodiment of the sample detector according to the present invention is illustrated in FIG. 3 in which the reference numeral 1 represents a carrier which is the same as that shown in FIG. 1 and on which a large number of samples 2 (fractionated patterns of sera) are arranged at definite intervals. The reference numeral 30 designates an optical fiber group consisting of a plural number of optical fibers 31, 32, . . . having light exit ends 31a, 32a, . . . so arranged as to make emerging light incident perpendicularly to the surface of the carrier and arranged in a row in the direction (x direction) perpendicular to the shifting direction of the carrier. The reference numeral 40 denotes a second optical fiber group consisting of optical fibers 41, 42, . . . in the same number as those of the first optical fiber group and having entrance ends 41a, 42a, . . . facing the exit ends 31a, 32a, . . . of the optical fibers 31, 32, . . . of the first optical fiber group 30. Therefore, the light emerging from the exit ends 31a, 32a, . . . of the individual optical fibers 31, 32, . . . of the first optical fiber group 30 is incident on the entrance ends 41a, 42a, . . . of the individual optical fibers 41, 42, . . . of the second optical fiber group 40. The exit ends 31a, 32a, . . . and entrance ends 41a, 42a, . . . of the individual optical fibers of both the optical fiber groups should desirably be arranged as close as possible to each other for preventing external light other than that emerging from the exit ends of the optical fibers from being incident on the entrance ends and for enhancing the signal-to-noise ratio. The reference numerals 51, 52, . . . represent light emitting diodes placed at the other ends (entrance ends) 31b, 32b, . . . of the individual optical fibers of the first optical fiber group 30, the reference numeral 60 designates a photo detector element arranged in the vicinity of the other ends (exit ends) 41b, 42b, . . . (bundled) of the individual optical fibers of the second optical fiber group 40 and the reference numeral 61 denotes a preamplifier. The light source assembly 3 for photometry consisting of the light source lamp 4, lens system 5, filter 6, slit plate 7, etc. and photometric detector assembly 8 are substantially the same as those shown in FIG. 1 and will not be described in detail.

Figure 4:
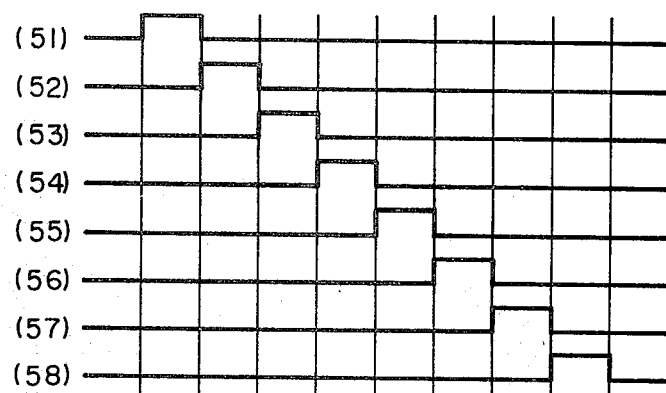
FIG. 4 shows a diagram illustrating the glowing timing of light emitting elements used in the sample detector according to the present invention.
Figure 5:
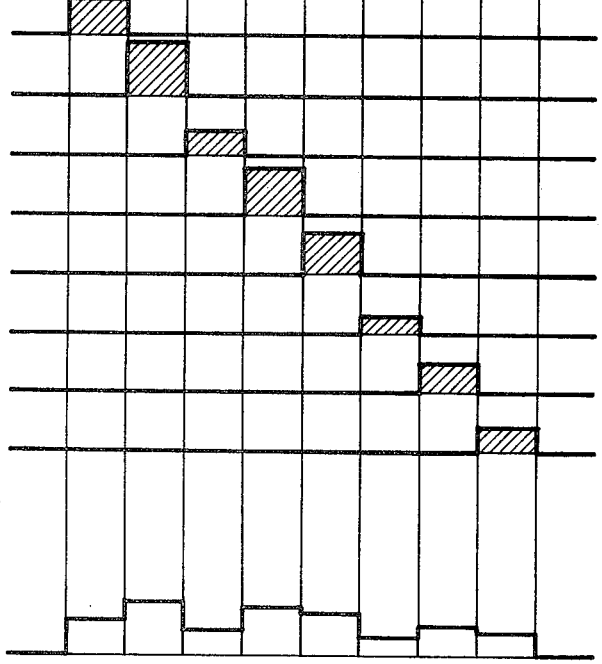
FIG. 5 illustrates a diagram showing an example of outputs from a photodetector element when the light emitting elements are caused to glow according to the glowing timing illustrated in FIG. 4.
Figure 6:
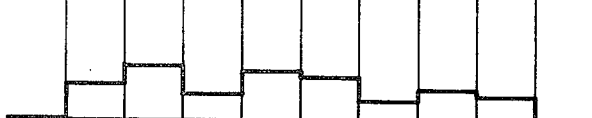
FIG. 6 illustrates a diagram showing outputs from a preamplifier based on the output illustrated in FIG. 5.

Now, the operation of the sample detector having the above-described construction according to the present invention will be described. First, the individual light emitting diodes 51, 52, . . . are caused to glow consecutively at a high speed as in the glowing timing diagram illustrated in FIG. 4 while shifting the carrier in the direction indicated by the arrow A. Description will be made of a sample detector comprising eight light emitting diodes, the first and second optical fiber groups consisting of eight optical fibers respectively as shown in the drawing which has no limitative significance. After all the light emitting diodes have been caused to glow starting, for example, from the light emitting diode 51, glowing is repeated in the sequence from the light emitting diodes 51, 52, . . . to the light emitting diode 58. The light emitted in this way from the light emitting diodes passes through the individual optical fibers 31, 32, . . . of the first optical fiber group 30, emerge from the exit ends 31a, 32a, . . . thereof, pass through the carrier 1, enter the entrance ends 41a, 42a, . . . of the corresponding optical fibers 41, 42, . . . of the second optical fiber group 40, pass through said optical fibers, emerge from the exit ends 41b, 42b, . . . thereof and is received by the photodetector element 60. Intensities of the received light correspond to the concentration of the sample applied onto the carrier, and outputs provided from the photo detector element based on the intensities of the received light can be exemplified as illustrated in FIG. 5. These outputs are totalized by the preamplifier 61 which provides outputs as shown in FIG. 6. Since the carrier is made transparent in this case, the light having passed through a portion free from any sample has high intensities, thereby providing high outputs from the preamplifier. When a sample passes between the ends of both the optical fiber groups which are arranged opposite to each other, in contrast, intensities of the light received by the photodetector element are attenuated in correspondence to the concentration of the sample, thereby lowering the output from the preamplifier.

For example, the preamplifier output corresponding to a portion free from any sample is as represented by the line $a_1$ in FIG. 7a, whereas the preamplifier output corresponding to a portion having a sample is as represented by the line $a_2$ in FIG. 7B. If a sample detection level is preset as indicated by a dashed line a in FIG. 7A and 7B respectively, outputs $a_1$ are higher than the level a when a sample is not present on the carrier, whereas at least one of outputs $a_2$ is lower than level a when a sample is present on the carrier. It is therefore possible to judge whether or not a sample is present on the carrier taking such a level a as standard. In other words, a turning point from a time at which the outputs produced from the light having passed through all the optical fibers are higher than the preset level of a to another time at which an output produced from light having passed through any one of the optical fibers is lower than the preset level, corresponds to the moment that a sample applied onto the carrier is just located between the ends of the optical fibers arranged in rows. Though the carrier is being shifted, output produced from the light having passed through any one of the optical fibers is lower than the preset level while a sample is located between the ends of the optical fibers arranged in rows. A time at which the outputs produced from the light having passed through all the optical fibers become higher than the preset level corresponds to the moment where the sample deviates from between the ends of the optical fibers arranged in rows. It is therefore possible to detect both the edges of a sample in this way. When the presence of a sample is detected as described above, it is possible to stop the carrier to locate the sample correctly at the position of the photometric apparatus in a definite time determined depending on the gaps as measured from the ends 31a, 32a, . . . and 41a, 42a, . . . of the optical fibers respectively to the photometric apparatus as well as the shifting speed of the carrier.

In FIG. 7A and FIG. 7B, the outputs are illustrated based on an assumption that they are kept constant when a transparent portion free from any sample of the carrier is located between the ends of both the optical fiber groups. In actuality, however, the outputs more or less vary due to the fact that the intensities of the light emitted from the individual light emitting diodes are different and that the transmittance to the individual optical fibers 31, 32, . . . and 41, 42, . . . is more or less different. Therefore, a more accurate judgment can be done when the outputs corresponding to the individual light emitting diodes are measured by glowing them before detecting samples. Correct output levels (corresponding to the level a shown in FIG. 7A and 7B) for the individual optical fibers are determined on the basis of the measured values, then these levels are stored as standards for judging the presence of samples. By presetting the standard levels as described above, it is possible not only to correct for differences in intensities of light emitted from the individual light emitting diodes and transmittance of the individual optical fibers but to compensate for variations of the entire detector system including drift of the electric circuit, etc. so as to assure sample detection with higher accuracy.

In detecting sample positions with the sample detector described above, data can be processed according to a computer program. Now, an explanation will be given for an example of means to feed image signals obtained through photoelectric conversion of the light received by the photodetector element after consecutively glowing the light emitting diodes into a computer in synchronization with the glowing timing of the light emitting diodes.

FIG. 8 illustrates a block diagram of a means to feed the image signals into a computer, wherein the image signals which have been subjected to photoelectric conversion with the photodetector element 60 are amplified by the preamplifier 61, whose outputs are converted by an A/D converter unit 62 into digital signals and the signals are fed into a computer 63 for storage. The reference numeral 64 represents an oscillator which is operated with an image detection command from the computer 63 and whose outputs are converted by a converter 65 into signals for glowing the individual light emitting diodes consecutively and fed into a driver circuit 66. The driver circuit 66 functions to cause the individual light emitting diodes to glow consecutively at definite time intervals.

Figure 9:
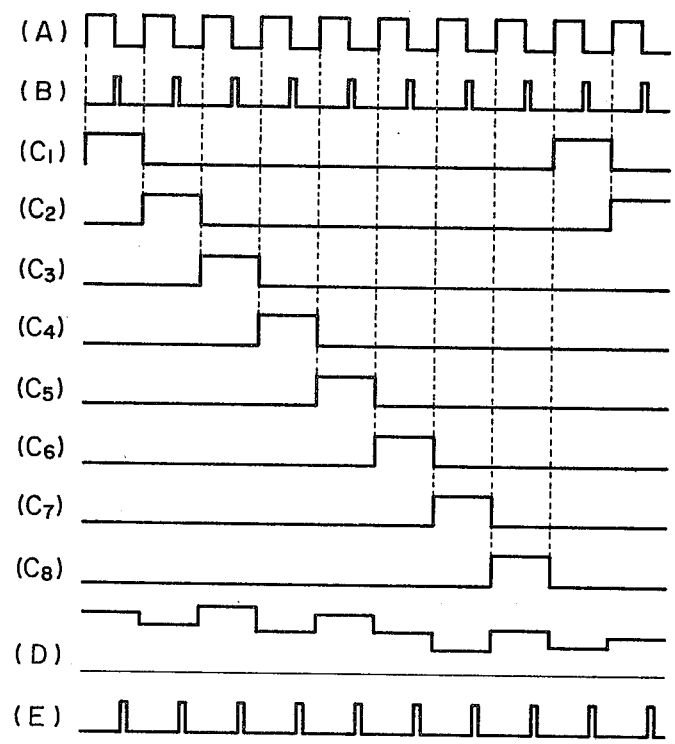
FIG. 9 shows a diagram illustrating outputs at the individual stages in the circuit shown in FIG. 8.

On the other hand, the outputs from the oscillator 64 are fed also into a one-shot multivibrator 67 which in turn provides an output as an A/D conversion command to the A/D converter unit. Upon receiving this output signal, the A/D converter unit 62 creates and outputs an A/D conversion end signal which is fed into the computer 63 for taking the data thereinto at that time. Since the light emitting diodes are caused to glow consecutively, it is possible to make the individual light emitting diodes correspond to the data in a relationship of 1:1 so as to identify each item of the data corresponding to each of the light emitting diodes. FIG. 9 illustrates a time chart clarifying the signal at each stage of the block diagram shown in FIG. 8. In FIG. 9, the reference symbol A represents oscillation signals provided from the oscillator, the reference symbol B designates output signals from the one-shot multivibrator 67 triggered at the falling end of the oscillation signal A and the reference numerals $C_1$ through $C_8$ denote driving signals for the individual light emitting diodes which are created based on the input of the oscillation signal A to the converter 65 for causing the individual light emitting diodes 51 through 58 to glow consecutively. The light emitted from the energized light emitting diodes is received by the photodetector element 60, converted into image signals through photoelectric conversion and amplified into signal D by the preamplifier 61. By taking this output signal D into the computer at the times determined based on the conversion end signal E created by the A/D converter unit, it is possible to input output signals corresponding to the individual light emitting diodes into the computer.

As is understood from the foregoing descriptions, the sample detector according to the present invention requires a single preamplifier in combination with a single photodetector element, and can be manufactured at low cost. Further, the sample detector according to the present invention assures highly accurate detection since it requires only a narrow photo sensitive area on the photo detector element. By using a larger number of optical fibers, said sample detector can easily detect widths and both edges of samples even when they have large areas, or detect samples easily and accurately even when the carrier is deviated in the back-forth direction or fed obliquely. Furthermore, since the sample detector according to the present invention uses optical fibers both on the light source side (the first optical fiber group) and on the detector side (the second optical fiber group), it assures higher flexibility in layout or arrangement of the light source and photo detector element as compared with the conventional examples in which photodetector elements are arranged in the vicinity of the carrier passage. Moreover, the sample detector according to the present invention permits accurate positional detection even when samples are applied onto a carrier at short intervals since it permits the arrangement, on the side of the carrier passage, of the ends of the optical fiber groups at positions very close to the photometric apparatus used as the main optical system of the sample detector.

In addition, the sample detector according to the present invention is capable of eliminating influence due to differences in transmittance of the individual optical fibers, and canceling variations in outputs caused with time lapse as well as electrical variations such as drift. Though the present invention has been described with reference to an embodiment using a single photodetector element, plural numbers of photodetector elements may be used as corresponding to several bundles of optical fibers by dividing the optical fibers of the second optical fiber group into a number of bundles of optical fibers at the exit ends thereof.

We claim:

1. A sample detector for monitoring a moving carrier, comprising:
   a first optical fiber group including a plural number of optical fibers arranged in a direction perpendicular to the moving direction of said carrier and having exit end surfaces adjacent to said carrier,
   a second optical fiber group including a plural number of optical fibers having entrance end surfaces arranged opposite to the exit end surfaces of said first optical fiber group and bundled exit end surfaces,
   a plural number of light emitting elements arranged in the vicinity of the entrance end surfaces of the individual optical fibers of said first optical fiber group,
   a photodetector element arranged in the vicinity of the bundled exit end surfaces of said second optical fiber group,
   a preamplifier connected to the output side of said photodetector element, said sample detector being so adapted as to detect the presence of samples applied onto said carrier based on outputs from said preamplifier, and photometric means arranged adjacent to said first and second optical fiber groups and being operative when a time determined by the spacing between said first and second optical fiber groups and said photometric means has passed after the position of a sample on said carrier has been detected.

2. A sample detector for monitoring a moving carrier, comprising:

a first optical fiber group including a plural number of optical fibers arranged in a direction perpendicular to the moving direction of said carrier and having exit end surfaces;

a second optical fiber group including a plural number of optical fibers having entrance end surfaces arranged opposite to the exit end surfaces of said first optical fiber group;

a plural number of light emitting elements arranged in the vicinity of the entrance end surfaces of the individual optical fibers of said first optical fiber group;

a photodetector element arranged in the vicinity of the exit end surfaces of said second optical fiber group;

a preamplifier connected to the output side of said photodetector element; and means for detecting an edge of a sample by detecting a turning point from a time at which said outputs from the preamplifier corresponding to all the light emitting elements are higher than a preset level to another time at which said outputs from the preamplifier corresponding to at least one of the light emitting elements is lower than said preset level, and for detecting the other edge of the sample by detecting a time at which said outputs from the preamplifier corresponding to all the light emitting elements are higher than said preset level once again.

3. A sample detector according to claim 2 further including means for energizing individual light emitting elements, and wherein the means for producing output signals representative of a preset level includes means for measuring the outputs from the preamplifier for each light emitting element and means for storing said measured outputs.

* * * * *